United States Patent [19]
DeSantis, Jr. et al.

[11] Patent Number: 5,480,900
[45] Date of Patent: Jan. 2, 1996

US005480900A

[54] COMBINATIONS OF PROSTAGLANDINS AND CLONIDINE DERIVATIVES FOR THE TREATMENT OF GLAUCOMA

[75] Inventors: Louis DeSantis, Jr., Fort Worth; Verney L. Sallee, Southlake, both of Tex.

[73] Assignee: Alcon Laboratories, Inc., Fort Worth, Tex.

[21] Appl. No.: 422,570

[22] Filed: Apr. 10, 1995

Related U.S. Application Data

[63] Continuation of Ser. No. 213,380, Mar. 14, 1994, abandoned, which is a continuation of Ser. No. 960,065, Oct. 13, 1992, abandoned.

[51] Int. Cl.$^6$ .................. A61K 31/415; A61K 31/215; A61K 31/19
[52] U.S. Cl. .................. 514/392; 514/530; 514/573; 514/913
[58] Field of Search .................. 514/530, 573, 514/392, 913

[56] References Cited

FOREIGN PATENT DOCUMENTS

0458589A1  11/1991  European Pat. Off. .

OTHER PUBLICATIONS

Kriegelstein, "Medikamentose Glaukomtherapie," *Fortschritte Der Ophthalmologie*, 87:172–174 (1990).

*Primary Examiner*—Zohreh Fay
*Attorney, Agent, or Firm*—James A. Arno; Barry L. Copeland; Julie J. L. Cheng

[57] ABSTRACT

Combinations of at least one clonidine derivative and at least one prostaglandin are used to treat glaucoma and ocular hypertension without some of the side effects typically associated with topical administration of prostaglandins.

20 Claims, No Drawings

COMBINATIONS OF PROSTAGLANDINS AND CLONIDINE DERIVATIVES FOR THE TREATMENT OF GLAUCOMA

CROSS REFERENCE TO RELATED APPLICATIONS

This application is a continuation of U.S. patent application Ser. No. 08/213,380, filed Mar. 14, 1994, now abandoned, which was a continuation of U.S. patent application Ser. No. 07/960,065 filed Oct. 13, 1992, now abandoned.

BACKGROUND OF THE INVENTION

1. Field of the Invention

The present invention relates generally to the field of ophthalmology. In particular, the invention relates to the treatment of glaucoma and ocular hypertension using a combination of at least one clonidine derivative (e.g., para-amino clonidine) and at least one prostaglandin.

2. Discussion of Related Art

Although the underlying causes of glaucoma are not understood, its symptoms often include elevated intraocular pressure, which may be caused either by over-production of aqueous humor or by inadequate outflow of aqueous humor. If left untreated, or if inadequately treated, glaucoma can lead to blindness or significant loss of vision. There is therefore a continuing need for therapies which control the elevated intraocular pressure associated with glaucoma.

There are currently a number of drugs utilized in the treatment of glaucoma, including: miotics (e.g., pilocarpine, carbachol and acetylcholinesterase inhibitors); sympathomimetics (e.g., epinephrine and dipivalylepinephrine); alpha-2 agonists (e.g., para-amino clonidine); beta-blockers (e.g., betaxolol, levobunolol and timolol); and carbonic anhydrase inhibitors (e.g., acetazolamide, methazolamide and ethoxzolamide). Miotics and sympathomimetics are believed to lower IOP by increasing the outflow of aqueous humor through the trabecular meshwork, while beta-blockers, alpha-2 agonists and carbonic anhydrase inhibitors are believed to lower IOP by decreasing the formation of aqueous humor.

In addition, although they have not yet been approved for anti-glaucoma therapy, certain classes of prostaglandins and prostaglandin analogues (hereinafter collectively referred to as "prostaglandins") have been shown in various animal models and in some clinical studies to reduce intraocular pressure (IOP) to a greater extent than most currently used therapeutic agents. See, for example: U.S. Pat. Nos. 4,097,489 (Bundy), 4,599,353 (Bito), 4,994,274 (Chan et al.) and EP 289 349 (Ueno et al.). In contrast to the case with miotics, prostaglandins are believed to lower IOP by increasing the outflow of aqueous humor via the uveo-scleral route. In addition, prostaglandins may possibly have other effects in the eye, such as enhancing vascular support of ocular tissues; however, there is no understanding of that mechanism at this time.

All six types of therapeutic agents have potentially serious side effects: miotics such as pilocarpine can cause blurring of vision and other, visual side effects, which may lead either to decreased patient compliance or to termination of therapy; carbonic anhydrase inhibitors can also cause serious side effects which affect patient compliance and/or necessitate the withdrawal of treatment; at least one beta-blocker, timolol, has increasingly become associated with serious pulmonary side effects attributable to its effect on beta-2 receptors in pulmonary tissue; and prostaglandins often produce hyperemia and edema of the conjunctiva, resulting in redness and hyperesthesia of the eye, which may affect patient compliance. In addition to these side effects, a therapy regimen which includes the use of two or more pharmaceutical compositions containing drugs selected from two or more of the above-cited classes requires the patient to apply the, compositions to the affected eye(s) in separate, spaced dosages, several times per day. Patient compliance with such complicated dosage regimens can be very poor, particularly in elderly patients. Since the majority of glaucoma patients are elderly, this patient compliance problem is significant.

In light of the foregoing circumstances, it is clear that a need exists for new, more potent anti-glaucoma compositions which avoid or reduce the above-cited side effects, while increasing patient compliance. The present invention is directed to such compositions.

SUMMARY OF THE INVENTION

It has unexpectedly been found that administration of one or more prostaglandins in combination with one or more clonidine derivatives controls or lowers intraocular pressure (IOP) without the accompanying inflammatory response (including hyperemia) typically found with prostaglandins. The present invention therefore provides compositions and methods useful for the treatment of glaucoma and ocular hypertension. The compositions contain a combination of at least one clonidine derivative and at least one prostaglandin which are effective in reducing or controlling IOP, and which have a reduction or elimination of the side effects normally associated with topical application of prostaglandins.

In a preferred formulatory embodiment of the compositions of the present invention, the above combinations may further include an anionic mucomimetic polymer, a gelling polysaccharide, a finely divided drug carrier substrate (defined below), or a combination of these components. These additional components provide compositions which are comfortable and have sustained release.

DETAILED DESCRIPTION OF THE INVENTION

The present invention utilizes combinations of at least one clonidine derivative and at least one prostaglandin to treat glaucoma and ocular hypertension.

Clonidine is a known hypotensive compound, and is described, for example, in U.S. Pat. No. 3,202,660 (Zeile et al.); the contents of this patent relating to the structure, preparation and physical properties of this compound are incorporated herein by reference. It is also known that certain clonidine derivatives are effective in lowering intraocular pressure when applied topically to the eye; this discovery is described in U.S. Pat. No. 4,461,904 (York, Jr.), the entire contents of which are incorporated herein by reference. The clonidine derivatives described in this patent are 2-(tri-substituted phenylimino)-imidazoline compounds, which are also known as 2-(tri-substituted anilino)-1,3-diazacyclopentene-(2) compounds. Reference is made to this patent for further details concerning the structure, preparation and physical properties of these clonidine derivatives. Related developments are described in U.S. Pat. Nos. 4,517,199 (York, Jr.), 4,587,257 (DeSantis et al.) and 4,515,800 (Cavero et al.); which are all incorporated herein by reference to the extent that they disclose, generically and specifically, the subject clonidine-like compounds.

A comprehensive discussion of the properties of clonidine and clonidine-like compounds is presented in a publication by Timmermans et al. entitled: "Structure-Activity Relationships in Clonidine-Like Imidazolidines and Related Compounds" (Gustav Fischer Verlag, New York: 1980, page 1–97). The entire contents of that publication are incorporated herein by reference. As indicated by Timmermans et al., the molecular structure of clonidine consists of three parts: an aromatic (i.e., aryl) portion, a bridge, and an imidazolidine moiety. Timmermans et al. disclose many compounds which have been produced by modifying one or two of these three parts, but which retain one of the three parts intact. For purposes of the present specification, all such compounds are defined as being "clonidine derivatives."

A preferred group of clonidine derivatives are those of formula:

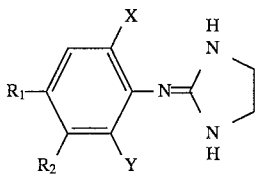

wherein: $R_1$ and $R_2$ are selected from H, OH, NHR' and

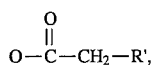

with R' being selected from H and $C_1$–$C_4$ alkyl, provided that one of $R_1$ and $R_2$ is hydrogen; and X and Y are selected from Br, Cl, $CH_3$ and $CH_2CH_3$.

Specific examples of Compounds from this group are set forth in Table 1, below.

TABLE 1

| Compound | $R_1$ | $R_2$ | X | Y |
|---|---|---|---|---|
| 1 | $NHCH_3$ | H | $CH_3$ | $CH_3$ |
| 2 | $NHCH_3$ | H | $CH_2CH_3$ | $CH_2CH_3$ |
| 3 | $NHCH_3$ | H | Cl | Cl |
| 4 | $NH_2$ | H | Br | Br |

A group of especially preferred clonidine derivatives of formula (I) are those in which $R_1$ and $R_2$ are selected from H and $NH_2$, provided that one of $R_1$ and $R_2$ is H, and X and Y are selected from Cl, $CH_3$, and $CH_2CH_3$. Specific examples of compounds from this group are set forth in Table 2, below.

TABLE 2

| Compound | $R_1$ | $R_2$ | X | Y |
|---|---|---|---|---|
| 5 | H | $NH_2$ | $CH_3$ | $CH_3$ |
| 6 | $NH_2$ | H | $CH_2CH_3$ | $CH_2CH_3$ |
| 7 | H | $NH_2$ | Cl | Cl |
| 8 | $NH_2$ | H | $CH_2CH_3$ | Cl |
| 9 | $NH_2$ | H | $CH_3$ | Cl |
| 10 | $NH_2$ | H | $CH_2CH_3$ | $CH_3$ |
| 11 | $NH_2$ | H | $CH_3$ | $CH_3$ |
| 12 | H | $NH_2$ | $CH_2CH_3$ | $CH_2CH_3$ |
| 13 | $NH_2$ | H | Cl | Cl |

Of these specific examples, Compound 13 para-amino clonidine (also known as apraclonidine), has been found to be particularly well-suited for use in the present invention.

A second preferred group of clonidine derivatives useful in the present invention are those of formula:

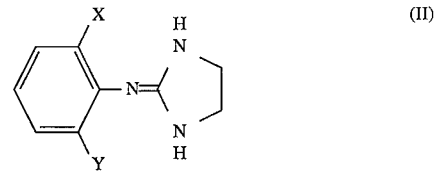

wherein: X and Y are selected from Br, Cl, $CH_3$ and $CH_2CH_3$, with the provision that at least one of X and Y is alkyl. Compounds of this type are described, for example in U.S. Pat. No. 3,468,887 (Stahle et al.), and *J. Med. Chem.*, 19: 1049–54 (1976). The contents of this patent and article relating to the structure, preparation and physical properties of these compounds are incorporated herein by reference. Specific examples of compounds from this group are set forth in Table 3, below.

TABLE 3

| Compound | X | Y |
|---|---|---|
| 14 | $CH_2CH_3$ | $CH_2CH_3$ |
| 15 | $CH_2CH_3$ | $CH_3$ |
| 16 | Cl | $CH_2CH_3$ |

In addition to the 2-(arylimino)imidazolidines identified above, other groups or classes of alpha-2 agonists which may be utilized in the present invention include 2-(arylimino)oxazolidines; 2-(arylmethylene) imidazolidines; 2-(arylimino) pyrrolidines; arylalkylaminoguanidines, such as aryl-imidazoquinazolines and phenyl-acetyguanidines; and 2-(phenylimino)diazocyclopentenes. All of these groups of drugs may be referred to as being clonidine derivatives or "clonidine-like" drugs.

The terms "prostaglandin" and "PG" are generally used to describe a class of compounds which are analogues and derivatives of prostanoic acid (III):

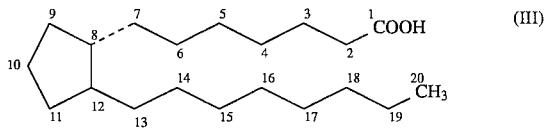

PG's may be further classified, for example, according to their 5-membered ring structure, using a letter designation:

Prostaglandins of the A series (PGA's): 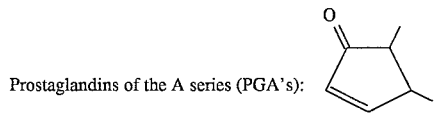

Prostaglandins of the B series (PGB's): 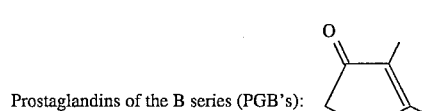

Prostaglandins of the C series (PGC's): 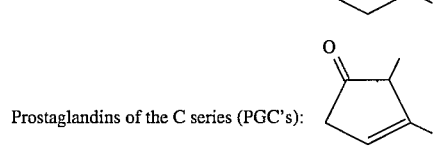

Prostaglandins of the D series (PGD's): 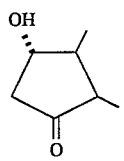

Prostaglandins of the E series (PGE's): 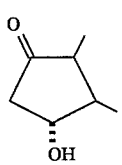

Prostaglandins of the F series (PGF's): 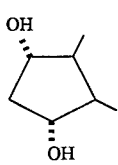

Prostaglandins of the J series (PGJ's): 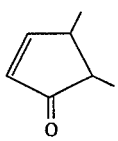

PG's may be further classified based on the number of unsaturated bonds on the side chain:

$PG_1$'s (13, 14- unsaturated):

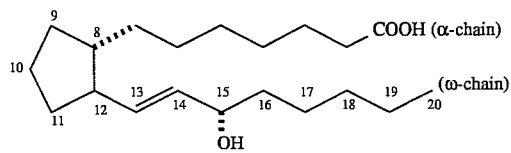

PG's (13, 14- and 5,6- unsaturated):

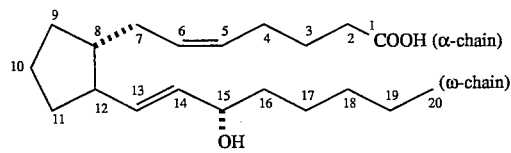

PG's (13, 14- 5, 6- and 17, 18- unsaturated):

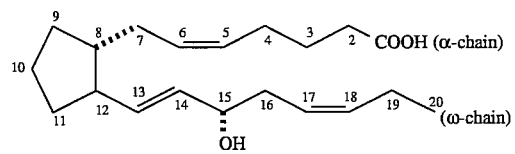

An historical review of the ocular effects of prostaglandins and other eicosanoids can be found in Bito, L. and J. Stjernschantz, *The Ocular Effect of Prostaglandins and Other Eicosanoids*, Alan R. Liss, Inc., New York: 1989, 1–13.

The prostaglandins which may be utilized in the present invention include all pharmaceutically acceptable prostaglandins, their derivatives and analogues, and their pharmaceutically acceptable esters and salts (hereinafter collectively referred to as "prostaglandins" or "PG's"), which are capable of reducing intraocular pressure when applied topically to the eye. Such prostaglandins include the natural compounds: $PGE_1$, $PGE_2$, $PGE_3$, $PGF_{1\alpha}$, $PGF_{2\alpha}$, $PGF_{3\alpha}$, $PGD_2$ and $PGI_2$ (prostacyclin), as well as analogues and derivatives of these compounds which have similar biological activities of either greater or lesser potencies. Analogues of the natural prostaglandins include but are not limited to: alkyl substitutions (e.g., 15-methyl or 16,16-dimethyl), which confer enhanced or sustained potency by reducing biological metabolism or alter selectivity of action; saturation (e.g., 13,14-dihydro) or unsaturation (e.g., 2,3-didehydro, 13,14-didehydro), which confer sustained potency by reducing biological metabolism or alter selectivity of action; deletions or replacements (e.g., 11-deoxy, 9-deoxo-9-methylene), which enhance chemical stability and/or selectivity of action; and ω-chain modifications (e.g., 18,19,20-trinor-17-phenyl, 17,18,19,20-tetranor-16-phenoxy), which enhance selectivity of action and reduce biological metabolism. Derivatives of these prostaglandins include all pharmaceutically acceptable salts and esters, which may be attached to the 1-carboxyl group or any of the hydroxyl groups of the prostaglandin by use of the corresponding alcohol or organic acid reagent, as appropriate. It should be understood that the terms "analogues" and "derivatives" include compounds which exhibit functional and physical responses similar to those of prostaglandins per se.

The following publications disclose examples of prostaglandins which are suitable for use in the present invention: Crabbe, P. (ed), "Prostaglandin Research," Academic Press, New York: 1977; *Advances in Prostaglandin, Thromboxane, and Leukotriene Research*, 14: 263–307 (1985); ibid., 14: 309–425 (1985); U.S. Pat. Nos. 3,884,969 (Schaub et al.); 3,873,607 (Bernady et al.); GB 1 444 971 (Floyd, Jr. et al.); U.S. Pat. Nos. 4,110,368 (Floyd, Jr. et al.); 4,291,175 (Wissner et al.); 4,321,405 (Weiss); 4,343,949 (Bernady et al.); 4,614,825 (Snitman et al.); 4,029,681 (Smith); 4,097,489 (Bundy); 4,288,616 (Sih); 3,755,426 (Strike et al.); 4,576,962 (Matthews); 4,599,353 (Bito); EP 364 417 (Stjernschantz et al.); DE 39 23 797 (Klar et al.); WO 85/02841 (Skuballa et al.); EP 299 914 (Buchmann et al.); EP 399 839 (Woodward et al.); U.S. Pat. No. 4,994,274 (Chan et al.); WO 91/14428 (Woodward); U.S. Pat. No. 5,093,329 (Woodward); EP 289 349 (Ueno et al.); and EP 366 279 (Ueno et al.). All of these publications are incorporated by reference herein with respect to their disclosures and teachings concerning prostaglandin structure, synthesis and activity. It is to be understood that the prostaglandins disclosed in and taught by the above-referenced publications are only exemplary in nature; the present invention is not intended to be limited by the disclosures and teachings of the above-referenced publications.

Specific examples of prostaglandins which are useful in the present invention include: $PGF_{2\alpha}$, $PGE_2$, $PGE_1$, prostacyclin, 15(S)-methyl-$PGF_{2\alpha}$, 16,16-dimethyl-$PGF_{2\alpha}$, 15(S)-methyl-$PGF_2$, 16,16-dimethyl-$PGF_2$, 17,18,19,20-tetranor-16-phenoxy-$PGF_2$, 17,18,19,20-tetranor-16-phenoxy-$PGF_{2\alpha}$, 18,19,20-trinor-17-phenyl-$PGE_2$, 18,19,20-trinor-17-phenyl-$PGF_{2\alpha}$, trimoprostil, RS-84-135, rioprostil, S-1033, S-747260, nocloprost, CS-412, YPG-209, K-10134, cloprostenol, fluprostenol, luprostiol, etiproston, tiaprost, SQ 27986, ZK 138519, ZK 118182, PhXA41, RO-221327, HR-466, HR-601, ONO-1206, 11-deoxy-$PGE_2$, 11-deoxy-$PGF_{2\alpha}$, 11-deoxy-16,16 -dimethyl-$PGE_2$, 11-deoxy-15(S)-methyl-$PGE_2$, 11-deoxy-15(S)-methyl-$PGF_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, as well as their pharmaceutically acceptable esters and salts, as appropriate for the respective individual structures. The most preferred prostaglandins are: $PGF_{2\alpha}$-1-isopropyl ester, $PGF_{2\alpha}$-1-ethyl ester, RO-229648, SQ 27986, ZK 138519, PhXA41 and 18,19,20-trinor-17-phenyl-$PGF_{2\alpha}$-1-methyl ester. All of the foregoing compounds are known.

In general, compositions of the present invention will include one or more clonidine derivatives in an mount between about 0.02 and about 2.0 percent by weight (wt %) and one or more prostaglandins in an amount between about 0.00001 and about 0.2 wt %. It is preferred to use one or more clonidine derivatives in an amount between about 0.05 and about 1.0 wt %, and it is especially preferred to use an amount between about 0.1 and about 0.25 wt %. It is preferred to use one or more prostaglandins in an amount between about 0.0001 and about 0.01 wt %, depending on the potency of the prostaglandin. The ratio by weight of clonidine derivative to prostaglandin is generally between about 1:1 to about 10,000:1 and preferably between about 5:1 to about 1000:1. It should be understood that the ratio by weight of clonidine derivative to prostaglandin will greatly depend on the potency of the prostaglandin used, since the potency of different prostaglandins may differ by as much as a factor of $10^5$.

In addition to the above-described principal active ingredients, the antiglaucoma compositions of the present invention may further comprise various formulatory ingredients, such as antimicrobial preservatives and tonicity agents. Examples of suitable antimicrobial preservatives include: benzalkonium chloride, thimerosal, chlorobutanol, methyl paraben, propyl paraben, phenylethyl alcohol, edetate disodium, sorbic acid, Polyquad®, Dymed® and other agents equally well known to those skilled in the art. Such preservatives, if utilized, will typically be employed in an amount between about 0.001 and about 1.0 wt %. Examples of suitable agents which may be utilized to adjust the tonicity or osmolality of the formulations include sodium chloride, potassium chloride, mannitol, dextrose, glycerine and propylene glycol. Such agents, if utilized, will be employed in an amount between about 0.1 and about 10.0 wt %.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. No. 4,911,920 (Jani et al.) and in U.S. patent application Ser. No. 07/676,146 filed Mar. 27, 1991. The entire contents of that patent and patent application are incorporated herein by reference.

The high molecular weight, anionic mucomimetic polymers useful in the present invention have a molecular weight between about 50,000 and 6 million daltons. The polymers are characterized as having carboxylic acid functional groups and preferably contain between 2 and 7 carbon atoms per functional group. The gels which form during preparation of the ophthalmic polymer dispersion have a viscosity between about 1,000 to about 300,000 centipoise (cps). Suitable polymers are carboxy vinyl polymers, preferably those called Carbomers, e.g., Carbopol® (B. F. Goodrich Co., Cleveland, Ohio). Specifically preferred are Carbopol® 934 and 940. Such polymers will typically be employed in an amount between about 0.05 and about 8.0 wt %, depending on the desired viscosity of the composition. Pourable liquid compositions generally comprise an amount of the polymer between about 0.05 and about 2.0 wt %.

As used herein, the term "finely-divided drug carrier substrate" (or "DCS") means finely-divided solids, colloidal particles, or soluble polymers and/or polyelectrolytes which are capable of selective adsorption or binding with drug molecules. Examples of DCS include, but are not limited to: finely divided silica, such as fumed silica, silicates and bentonites; ion exchange resins, which can be anionic, cationic or non-ionic in nature; and soluble polymers, such as, alginic acid, pectin, soluble carrageenans, Carbopol®, and polystyrene sulfonic acid. In general, the DCS component is used at a level in the range of about 0.05 to about 10.0 wt %. For particulate DCS, the average particle size diameter ranges from 1 to 20 microns. The amount of DCS and its characteristics (e.g., amount of cross-linking, particle size) may be varied in order to produce the desired time-release profile for the chosen drug.

Preferred DCS are the ion exchange resins. Some resins which are used in chromatography make ideal DCS for binding drugs in the compositions of the present invention. Such resins are readily available, for example, from Rohm & Haas (Philadelphia, Pa.) under the name Amberlite® and from Dow Chemical Co. (Midland, Mich.) under the name Dowex®. The average particle size of the commercially available forms of the resins is about 40 to 150 microns. As the particle size of the resin is critical, such commercially available particles are most conveniently reduced to a particle size range of about 1.0 to 25 microns by ball milling, according to known techniques. At least 95% of the resulting spheroidal particles must have a diameter less than 20 microns. The ion exchange resins will typically be present in an amount between about 0.05 and about 10.0 wt % and will have an average particle size diameter between about 1 and about 20 microns.

As will be appreciated by those skilled in the art, the compositions may be formulated in various dosage forms suitable for topical ophthalmic delivery, including solutions, suspensions, emulsions, gels and erodible solid ocular inserts. The compositions are preferably aqueous, have a pH between 3.5 to 8.0 and an osmolality between 280 to 320 milliOsmoles per kilogram (mOsm/kg).

The compositions of the present invention may also comprise non-aqueous formulations such as: substantially non-aqueous liquids, substantially non-aqueous semi-solid compositions and solid compositions or devices. The first class, substantially non-aqueous liquids, comprise a combination of a clonidine derivative of formula (I) and at least one prostaglandin ("drug combination") dissolved or suspended in one or more of the following: vegetable and mineral oils, such as, liquid petrolatum, corn oil, castor oil, sesame oil and peanut oil; triglycerides, such as the capric/caprylic triglycerides commonly used in foods and cosmetics; liquid lanolin and lanolin derivatives; and perfluorohydrocarbons. The second class, semi-solid compositions, comprise a drug combination dissolved or suspended in one or more of the following: various types of petrolatum, such as white, yellow, red and so on; lanolin and lanolin derivatives; gelled mineral oil having a hydrocarbon base, such as Plastibase®; petrolatum and ethylene carbonate mixtures; petrolatum in combination with surfactants and polyglycol, such as polyoxyl 40 stearate and polyethylene glycol.

The third class, solid compositions or devices, include non-erodible devices which are inserted into the conjunctival sac of the eye and later removed, such as the Alza-type diffusion or osmotic pressure controlled polymer membranes; and bioerodible polymers which do not have to be removed from the conjunctival sac, such as essentially anhydrous but water soluble polymers and resins (e.g., celluloses, polycarboxylic acids, and so on). Especially preferred are the bioerodible inserts described and detailed in U.S. Pat. Nos. 4,540,408 (Lloyd) and 4,730,013 (Bondi et al.), wherein drug combinations of the present invention would be entrained in a non-aqueous matrix consisting essentially of polyvinyl alcohol. The entire contents of these two patents are incorporated herein by reference.

The present invention is also directed to methods of treating glaucoma and other ophthalmic diseases and abnormalities. The methods comprise topically applying to the affected eye(s) of the patient a therapeutically effective amount of a composition according to the present invention. The frequency and amount of dosage will be determined by the clinician based on various clinical factors. The methods will typically comprise topical application of one or two drops (approximately 30 microliters) of a liquid composition, or an equivalent amount of a solid or semi-solid dosage form, to the affected eye one to two times per day.

The invention has been i described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

What is claimed is:

1. A topical ophthalmic composition for the treatment of glaucoma, without significant inflammatory response, comprising a combination of a pharmaceutically effective amount of a prostaglandin and a pharmaceutically effective amount of a clonidine derivative.

2. The composition of claim 1, wherein the clonidine derivative is selected from the group consisting of:

a) a compound of formula:

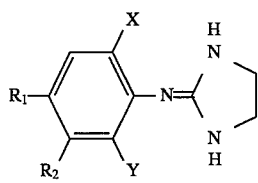

wherein:

$R_1$ and $R_2$ are selected from H, OH, NHR' and

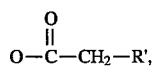

with R' being selected from H and $C_1$–$C_4$ alkyl, provided that one of $R_1$ and $R_2$ is hydrogen; and X and Y are selected from Br, Cl, $CH_3$ and $CH_2CH_3$; and b) a compound of formula:

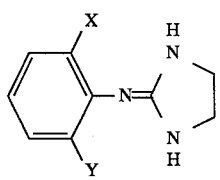

wherein:

X and Y are selected from Br, Cl, $CH_3$ and $CH_2CH_3$, with the provision that at least one of X and Y is alkyl.

3. The composition of claim 1, wherein the final composition concentration of clonidine derivative is between about 0.02 and about 2.0 wt % and the final composition concentration of prostaglandin is between about 0.00001 and about 0.2 wt %.

4. The composition of claim 3, wherein the final composition concentration of clonidine derivative is between about 0.05 and about 1.0 wt %.

5. The composition of claim 4, wherein the final composition concentration of clonidine derivative is between about 0.1 and about 0.25 wt %.

6. The composition of claim 3, wherein the final composition concentration of prostaglandin is between about 0.0001 and about 0.01 wt %.

7. The composition of claim 1, wherein the prostaglandin is selected from the group consisting of: $PGF_{2\alpha}$, $PGE_2$, $PGE_1$, prostacyclin, 15(S)-methyl-$PGF_{2\alpha}$, 16,16-dimethyl-$PGF_{2\alpha}$, 15(S)-methyl-$PGE_2$, 16,16-dimethyl-$PGE_2$, 17,18,19,20-tetranor-16-phenoxy-$PGE_2$, 17,18,19,20-tetranor-16-phenoxy-$PGF_{2\alpha}$, 18,19,20-trinor-17-phenyl-$PGE_2$, 18,19,20-trinor-17-phenyl-$PGF_{2\alpha}$, trimoprostil, RS-84-135, rioprostil, S-1033, S-747260, nocloprost, CS-412, YPG-209, K-10134, cloprostenol, fluprostenol, luprostiol, etiproston, tiaprost, SQ 27986, ZK 138519, ZK 118182, PhXA41, RO-221327, HR-466, HR-601, ONO-1206, 11-deoxy-$PGE_2$, 11-deoxy-$PGF_{2\alpha}$, 11-deoxy-16,16-dimethyl-$PGE_2$, 11-deoxy-15(S)-methyl-$PGE_2$, 11-deoxy-15(S)-methyl-$PGF_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, and their pharmaceutically acceptable esters and salts, as appropriate.

8. The composition of claim 7, wherein the prostaglandin is selected from the group consisting of: $PGF_{2\alpha}$-1-isopropyl ester, $PGF_{2\alpha}$-1-ethyl ester, RO-229648, SQ 27986, ZK 138519, PhXA41 and 18,19,20-trinor-17-phenyl-$PGF_{2\alpha}$-1-methyl ester.

9. The composition of claim 1, further comprising an anionic, mucomimetic polymer and a finely divided drug carrier substrate.

10. The composition of claim 9, wherein: the final composition concentration of clonidine derivative is between about 0.02 and about 2.0 wt % and the final composition concentration of prostaglandin is between about 0.00001 and about 0.2 wt %; the final composition concentration of anionic, mucomimetic polymer is between about 0.05 and about 8.0 wt %; and the final composition concentration of finely divided drug carrier substrate is between about 0.05 and 10.0 wt %.

11. The composition of claim 9, wherein the clonidine derivative is selected from the group consisting of:

a) a compound of formula:

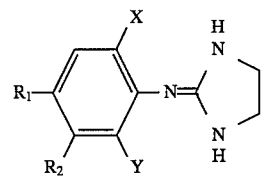

wherein:

$R_1$ and $R_2$ are selected from H, OH, NHR' and O-C-$CH_2$-R',

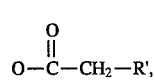

with R' being selected from H and $C_1$–$C_4$ alkyl, provided that one of $R_1$ and $R_2$ is hydrogen; and X and Y are selected from Br, Cl, $CH_3$ and $CH_2CH_3$; and b) a compound of formula:

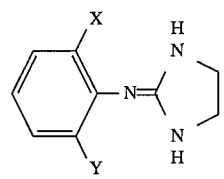
(II)

wherein:

X and Y are selected from Br, Cl, CH$_3$ and CH$_2$CH$_3$, with the provision that at least one of X and Y is alkyl.

12. The composition of claim 9, wherein the prostaglandin is selected from the group consisting of: PGF$_{2\alpha}$, PGE$_2$, PGE$_1$, prostacyclin, 15(S)-methyl-PGF$_{2\alpha}$, 16,16-dimethyl-PGF$_{2\alpha}$, 15(S)-methyl-PGE$_2$, 16,16-dimethyl-PGE$_2$, 17,18,19,20-tetranor- 16-phenoxy-PGE$_2$, 17,18,19,20-tetranor-16-phenoxy-PGF$_{2\alpha}$, 18,19,20-trinor-17-phenyl-PGE$_2$, 18,19,20-trinor-17-phenyl-PGF$_{2\alpha}$, trimoprostil, RS-84-135, rioprostil, S-1033, S-747260, nocloprost, CS-412, YPG-209, K-10134, cloprostenol, fluprostenol, luprostiol, etiproston, tiaprost, SQ 27986, ZK 138519, ZK 118182, PhXA41, RO-221327, HR-466, HR-601, ONO-1206, 11-deoxy-PGE$_2$, 11-deoxy-PGF$_{2\alpha}$, 11-deoxy-16,16-dimethyl-PGE$_2$, 11-deoxy-15(S)-methyl-PGE$_2$, 11-deoxy-15(S)-methyl-PGF$_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, and their pharmaceutically acceptable esters and salts, as appropriate.

13. The composition of claim 1, further comprising a gelling polysaccharide and a finely divided drug carrier substrate.

14. The composition of claim 13, wherein: the final composition concentration of clonidine derivative is between about 0.02 and about 2.0 wt % and the final composition concentration of prostaglandin is between about 0.00001 and about 0.2 wt %; the final composition concentration of gelling polysaccharide is between about 0.1 to about 3.0 wt %; and the final composition concentration of finely divided drug carrier substrate is between about 0.05 and 10.0 wt %.

15. The composition of claim 14, wherein the clonidine derivative is selected from the group consisting of:

a) a compound of formula:

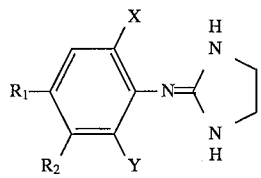
(I)

wherein:

R$_1$ and R$_2$ are selected from H, OH, NHR' and

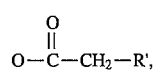

with R' being selected from H and C$_1$–C$_4$ alkyl, provided that one of R$_1$ and R$_2$ is hydrogen; and X and Y are selected from Br, Cl, CH$_3$ and CH$_2$CH$_3$; and b) a compound of formula:

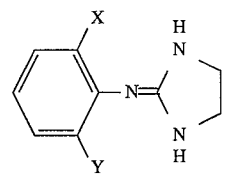
(II)

wherein:

X and Y are selected from Br, Cl, CH$_3$ and CH$_2$CH$_3$, with the provision that at least one of X and Y is alkyl.

16. The composition of claim 14, wherein the prostaglandin is selected from the group consisting of: PGF$_{2\alpha}$, PGE$_2$, PGE$_1$, prostacyclin, 15(S)-methyl-PGF$_{2\alpha}$, 16,16-dimethyl-PGF$_{2\alpha}$, 15(S)-methyl-PGE$_2$, 16,16-dimethyl-PGE$_2$, 17,18,19,20-tetranor-16-phenoxy-PGE$_2$, 17,18,19,20-tetranor- 16-phenoxy-PGF$_{2\alpha}$, 18,19,20-trinor-17-phenyl-PGE$_2$, 18,19,20-trinor-17-phenyl-PGF$_{2\alpha}$, trimoprostil, RS-84-135, rioprostil, S-1033, S-747260, nocloprost, CS-412, YPG-209, K-10134, cloprostenol, fluprostenol, luprostiol, etiproston, tiaprost, SQ 27986, ZK 138519, ZK 118182, PhXA41, RO-221327, HR-466, HR-601, ONO-1206, 11-deoxy-PGE$_2$, 11-deoxy-PGF$_{2\alpha}$, 11-deoxy-16,16-dimethyl-PGE$_2$, 11-deoxy-15(S)-methyl-PGE$_2$, 11-deoxy-15(S)-methyl-PGF$_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, and their pharmaceutically acceptable esters and salts, as appropriate.

17. A method of treating glaucoma, without significant inflammatory response, comprising applying to an affected eye a pharmaceutically effective amount of a prostaglandin and a pharmaceutically effective amount of a clonidine derivative.

18. The method of claim 17, wherein the clonidine derivative is selected from the group consisting of:

a) a compound of formula:

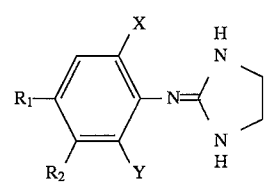
(I)

wherein:

R$_1$ and R$_2$ are selected from H, OH, NHR' and

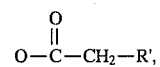

with R' being selected from H and C$_1$–C$_4$ alkyl, provided that one of R$_1$ and R$_2$ is hydrogen; and X and Y are selected from Br, Cl, CH$_3$ and CH$_2$CH$_3$; and b) a compound of formula:

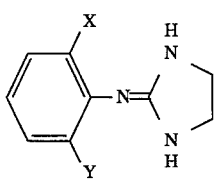

wherein:

X and Y are selected from Br, Cl, CH$_3$ and CH$_2$CH$_3$, with the provision that at least one of X and Y is alkyl.

19. The method of claim 17, wherein the prostaglandin is selected from the group consisting of: PGF$_{2\alpha}$, PGE$_2$, PGE$_1$, prostacyclin, 15(S)-methyl-PGF$_{2\alpha}$, 16,16-dimethyl-PGF$_{2\alpha}$, 15(S)-methyl-PGE$_2$, 16,16-dimethyl-PGE$_2$, 17,18,19,20-tetranor-16-phenoxy-PGE$_2$, 17,18,19,20-tetranor-16-phenoxy-PGF$_{2\alpha}$, 18,19,20-trinor-17-phenyl-PGE$_2$, 18,19,20-trinor-17-phenyl-PGF$_{2\alpha}$, trimoprostil, RS-84-135, rioprostil, S-1033, S-747260, nocloprost, CS-412, YPG-209, K-10134, cloprostenol, fluprostenol, luprostiol, etiproston, tiaprost, SQ 27986, ZK 138519, ZK 118182, PhXA41, RO-221327, HR-466, HR-601, ONO-1206, 11-deoxy-PGE$_2$, 11-deoxy-PGF$_{2\alpha}$, 11-deoxy-16,16-dimethyl-PGE$_2$, 11-deoxy-15(S)-methyl-PGE$_2$, 11-deoxy-15(S)-methyl-PGF$_{2\alpha}$, misoprostol, enisoprost, MDL-646, CL-115,574, CL-115,347, TR-4161, TR-4752, TR-4367, CP-27987, sulprostone, gemeprost, alfaprostol, delprostenate, prostalene, fenprostalene, CL-116,069, ONO-995, RO-229648, and their pharmaceutically acceptable esters and salts, as appropriate.

20. The method of claim 17, wherein between about 0.02 and about 2.0 wt % of clonidine derivative and between about 0.00001 and about 0.2 wt % of prostaglandin are applied to the affected eye.

\* \* \* \* \*